United States Patent [19]

Karimian

[11] Patent Number: 5,319,141

[45] Date of Patent: Jun. 7, 1994

[54] PROCESS OF MAKING NADOLOL

[75] Inventor: Khashayar Karimian, Brantford, Canada

[73] Assignee: Acic (Canada) Inc., Brantford, Canada

[21] Appl. No.: 675,907

[22] PCT Filed: Sep. 25, 1990

[86] PCT No.: PCT/CA90/00316

§ 371 Date: May 20, 1991

§ 102(e) Date: May 20, 1991

[87] PCT Pub. No.: WO91/04244

PCT Pub. Date: Apr. 4, 1991

[30] Foreign Application Priority Data

Sep. 25, 1989 [CA] Canada ................. 612.845-9

[51] Int. Cl.$^5$ .................. C07C 213/00; C07C 217/38
[52] U.S. Cl. ..................................... 564/349
[58] Field of Search ......................... 564/349

[56] References Cited

U.S. PATENT DOCUMENTS 2,687,435  8/1954  Woodward ................. 568/346
3,935,267  1/1976  Hauck et al. ............... 564/349

FOREIGN PATENT DOCUMENTS 882705   10/1971  Canada .
979912   12/1975  Canada .
979926   12/1975  Canada .
1000287  11/1976  Canada .
1041544  10/1978  Canada .
1059147   7/1979  Canada .
1063120   9/1979  Canada .
1064965  10/1979  Canada .
1132560   9/1982  Canada .
1260008   9/1989  Canada .
0138575   4/1985  European Pat. Off. .
2258995   6/1973  Fed. Rep. of Germany .
2421549  11/1974  Fed. Rep. of Germany .

OTHER PUBLICATIONS

Mangoni et al, Tetrahedron Letters, No. 5 (1973) pp. 4485-4486.

Primary Examiner—Richard L. Raymond
Attorney, Agent, or Firm—Ivor M. Hughes; Neil H. Hughes

[57] ABSTRACT

A process for making 5-(d-3-(tert-butylamino)-2-hydroxypropoxy)-1,2,3,4-tetrahydro-1-cis-2,3 naphthalenediol of the formula

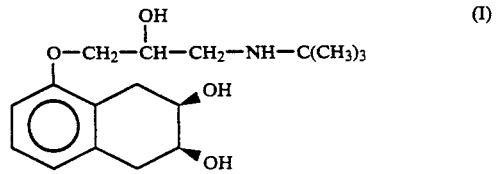

by reacting

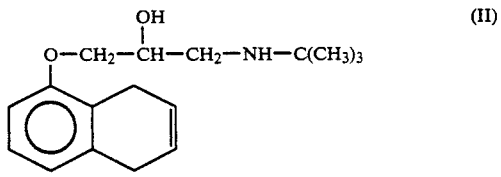

in an essentially water free environment with
(a) M'IO$_3$ wherein M' represents a suitable ion for forming the salt.
(b) I$_2$ (iodine)
(c) CH$_3$COO$^-$M''$^+$ wherein M'' represents a suitable ion for forming the salt
(d) glacial acetic acid and
(e) ROH/M'''OH where R is alkyl and M''' is a suitable metal ion.

13 Claims, No Drawings

PROCESS OF MAKING NADOLOL

FIELD OF INVENTION

This invention relates to a process for manufacturing 5-[d-3-(tert-butylamino)-2-hydroxypropoxy]-1,2,3,4-tetrahydro-1-cis-2,3 naphthalenediol, (Nadolol) a β-blocking agent having anti-arrhythmic activity and β-blocking activity.

BACKGROUND OF THE INVENTION

According to the Official Monograph of USP XXI, Nadolol is identified as follows:

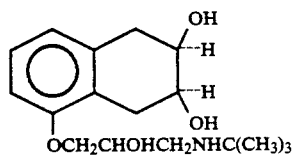

OCH$_2$CHOHCH$_2$NHC(CH$_3$)$_3$

Formula C$_{17}$H$_{27}$NO$_4$ M.W. 309.41; 2,3-Naphthalenediol, 5-[-3(1,1-dimethylethyl)amino]-2-hydroxypropoxy]-1,2,3,4-tetrahydro-, cis, 1-(tert-Butylamino)-3-[(5,6,7,8-tetrahydro-cis-6,7-dihydroxy-1-naphthyl)oxy]-2-propanol [42200-33-9]. Nadolol contains not less than 98.0 percent and not more than 101.5 percent of C$_{17}$H$_{27}$NO$_4$, calculated on a dried basis. Nadolol is also made up of 4 cis isomers.

Many processes have been proposed for the manufacture of Nadolol from various intermediates. There are 4 cis isomers of Nadolol and because each cis isomer of Nadolol produced may have a number of impurities associated with it (from the manufacturing process). Also some of the impurities in the starting materials may themselves become involved in the reaction (the starting materials may only be 80%-85% pure and some of the impurities may be unknowns). Thus, the Official Monograph provides the specifications for Nadolol, and assay procedures for determination of its purity. The Monograph does-not include an HPLC method.

A number of proposals have been made for making Nadolol. See Canadian Letters Patent 979,912; 979,926; 1,000,287; 1,041,544; 1,059,147; 1,063,120; and 1,064,965. Hauck has also proposed processes for separation of the four cis isomers from one another. (See Canadian Letters Patent 1,041,544; 1,059,147 and 1,064,965.) However the processes led to very low yields and are therefore not commercially viable.

Canadian Letters Patent 1,132,560 (Ciba-Geigy) discloses a process for inverting the configuration in optically active compounds characterized in that an optically active compound of the formula

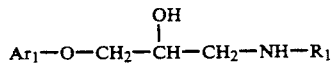

having a R(+) or S(−) configuration is converted by treating with concentrated phosphoric acid or concentrated sulphuric acid or a chloride or bromide of such acids, into an optically active compound and the resulting compound is hydrolyzed to form a compound with a configuration opposite to that of the starting material used. This process is complex.

It is therefore an object of this invention to provide an improved process for manufacturing 5-[d-3-(tert-butylamino)-2-hydroxypropoxy]-1,2,3,4-tetrahydro-1-cis-2,3 naphthalenediol in good yields.

Canadian Letters Patent 882,705 discloses a process for the preparation of

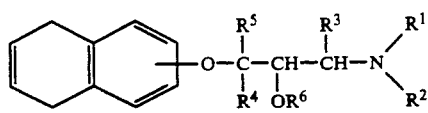

Applicant is also aware of the following additional publications (a) "A Convenient Procedure for the Cis-hydroxylation of Olefins" by L. Mangoni et al, Tetrahedron Letters No. 45, pp.4485–4486, 1973; and (b) "A Convenient Modification of the Woodward cis-hydroxylation of Olefins" L. Mangoni et al, Gazz. Chim. Ital. 1975, 105,377.

Woodward in U.S. Pat. No. 2,687,435 (1954) and at J. Am. Chem. Soc. 80,209 (1958) with F. V. Brutcher taught the hydroxylation of an olefin with iodine and silver acetate in wet acetic acid to give cis-glycols. The process involves the "trans" addition of iodine and silver acetate to give a "trans" -iodo-acetoxy-derivative. The latter is hydrolyzed to a cis- mono-glycol acetate with acetic acid and water. Alkaline hydrolysis results in the final cis-glycol.

Brutcher and Evans reported in Journal of Organic (1957) 23, 618, a modification to the process proposed by Woodward and Brutcher. This modification involved the interaction of an olefin with iodine, silver acetate, and wet acetic acid to give cis hydroxy acetate in one operation. Subsequent hydrolysis was purported to yield the free diol.

Bunton and Carr in an article "The hydroxylation of Cyclic Olefins by Iodine and Silver Acetate", J. Chem. Society (1963) 770 reported results as follows:

"Cyclohexenes.- The Woodward procedure, reaction between 1, 2-dimethylcyclohexene and iodine and silver acetate in 'wet' acetic acid (1.5% of water), gave after vacuum-distillation of the product and its recrystallization a 1:1 molecular compound of the cis-and the trans-diol. Stereospecific cis-hydroxylation by this method has been reported previously.[3] Reaction in 'dry' acetic acid gave no 1, 2-diol.

We therefore studied the oxidation of 1methylcyclohexene by the Woodward procedure and obtained the cis-1,2-diol. In agreement with other workers, we also obtained the cis-diol from cyclohexene by the Woodward procedure and the 'trans-diol by using 'dry' acetic acid.

Cyclopentenes. - The reaction between cyclopentene and iodine and silver acetaic in 'wet' acetic acid is reported to give the cis-diol in a 48% yield. By this method we converted 1-methylcyclopentene into the cis-diol in 20% yield, but obtained no diol from 1,2-dimethylcyclopentene."

Subsequently Hauck in Canadian Letters Patent 1,041,544 attempted to separate the four optical cis isomers of 2,3-cis-1,2,3,4-tetrahydro-S-[2-hydroxy-3-(tert-butylamino) propoxy]-2,3-naphthalenediol in order to determine the best of these isomers. The processes of manufacture (See pages 4, 5 and 6 of the Patent and example 4 at pages 18 and of the patent) employ water. Crystallization of isomer product is from chloroform. In Hauck's laboratory procedure resulting 1-(2,3-epoxypropoxy)-5,8-dihydronaphthalene is isolated and subsequently reacted with t-butylamine in a high pressure reactor. The resulting dl-1-(tert-butylamino)-3-(5,8-dihydronaphthyl)oxyl-2-propanol is then cis hydroxylated with wet acetic acid, silver iodide, and the resulting acetoxy iodide is hydrolysed with base and finally subjected to catalytic hydrogenation to afford crude Nadolol.

Mangoni et al in an article entitled "A convenient Modification of the Woodward cis-Hydroxylation of Olefins" (Gazz. Chem. Ital. 1975, 105, 377) discussed modifications of the Woodward procedure by subtituting for silver acetate. Wet acetic acid is still used; glacial acetic acid was also tried. No exceptional results are produced by the use of the glacial acetic acid. The cis-diol steroid product is produced with both procedures—in a slightly lesser percentage return using glacial acetic acid than a solution of acetic acid and water.

It is therefore another object of this invention to provide improved processes for the manufacture of Nadolol which unexpectedly yielded Nadolol in a minimal number of process steps, in good yields and Nadolol of substantial purity.

Further and other objects of this invention will be realized by those skilled in the art from the following summary of invention and detailed description of an embodiment thereof.

SUMMARY OF THE INVENTION

Unexpectedly, according to one aspect of the invention, there is provided a process for making very pure 5-[d-3-(tert-butylamino)-2-hydroxypropoxy]-1,2,3,4-tetrahydro-1-cis-2,3 naphthalenediol of the formula

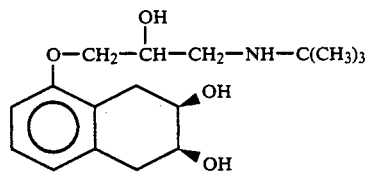

by reacting

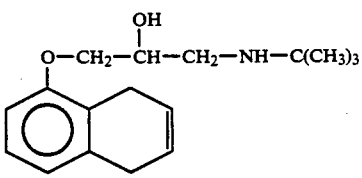

in an essentially water free environment with
  (a) M' $IO_3$ for example $KIO_3$(potassium iodate) or other suitable salt wherein M' represents a suitable ion for forming the salt (for example $Na^+, K^+$, etc);
  (b) $I_2$ (iodine)-a solid;
  (c) $CH_3COO^-M''^+$ for example $CH_3COO^-K^+$ (potassium acetate) or other suitable salt wherein M'' represents a suitable ion for forming the salt (for example $Na^+$, $K^+$, etc.)
  (d) glacial acetic acid
  and (e) ROH/M'''OH where R may be an alkyl radial (for example $CH_3$) and M''' is a suitable metal ion (for example $Na^+$, $K^+$, etc.).

This solution may then be evaporated and the residue treated with a solvent for example toluene, chloroform or a ketone of the formula $R_1COR_2$, wherein $R_1$ may be $CH_3$ and $R_2$ may be a higher alkyl group for the recovery of 5-[d-3-(tert-butylamino)-2-hydroxypropoxy]-1, 2, 3, 4 -tetrahydro-1-cis-2,3naphthalenediol. Compound II (shown at page 5 herein) may be made in accordance with the teachings of Canadian Letters Patent 882,705 (which involves isolation of intermediates and the use of a high pressure reactor at 50 psi) or any other suitable process including a process developed by the Applicant according to the following flow diagram in which isolation of the intermediates and the use of high pressure reactors are avoided:

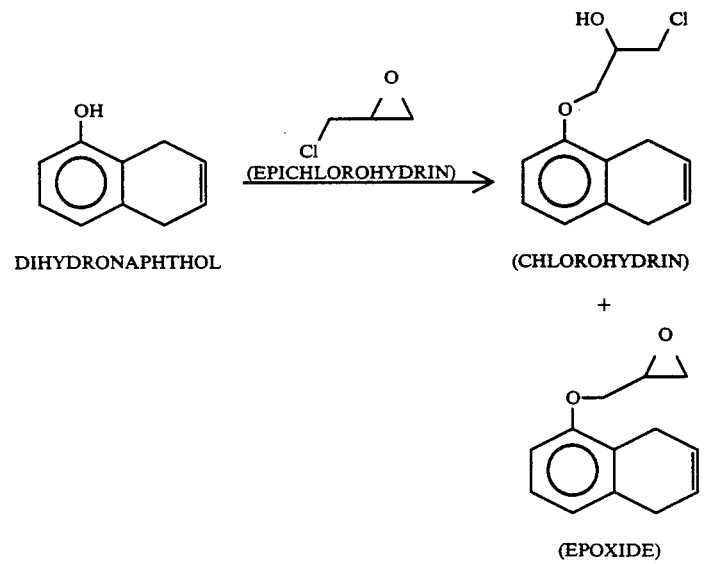

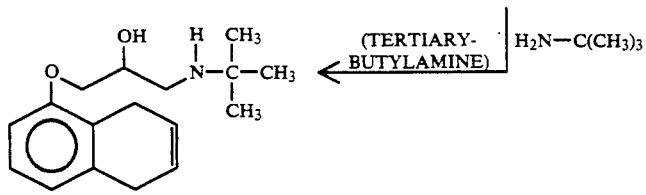

Thus a Production Scheme for Nadolol in one vessel (not a high pressure reactor) may comprise the following [without isolation of any intermediates]:

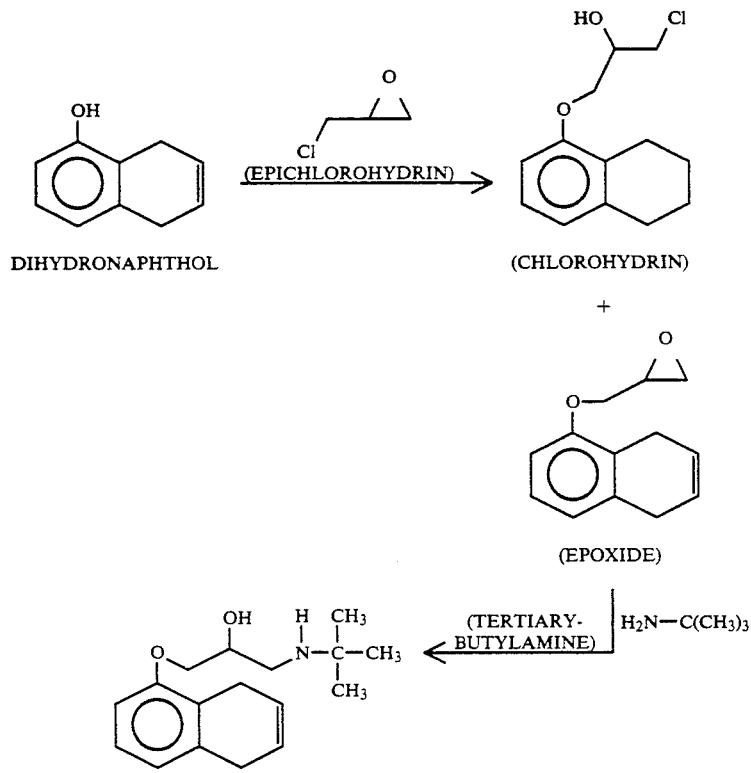

to which has been added (A) (GLACIAL ACETIC ACID)
(B) (IODINE)
(C) (M' IO$_3$ WHEREIN M' REPRESENTS A SUITABLE ION FOR FORMING THE SALT)
(D) (CH$_3$COOM" WHEREIN M" REPRESENTS A SUITABLE ION FOR FORMING THE SALT)
(E) ROH/M'" OH WHEREIN R MAY BE AN ALKYL RADIAL AND M'" IS A SUITABLE METAL ION FOR FORMING THE FINAL PRODUCT

} WATER FREE ENVIRONMENT

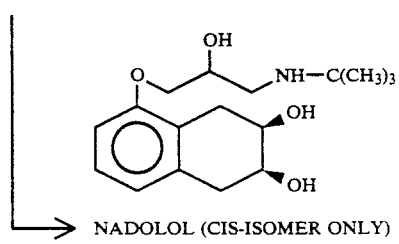

NADOLOL (CIS-ISOMER ONLY)

A more detailed Production Scheme is as follows

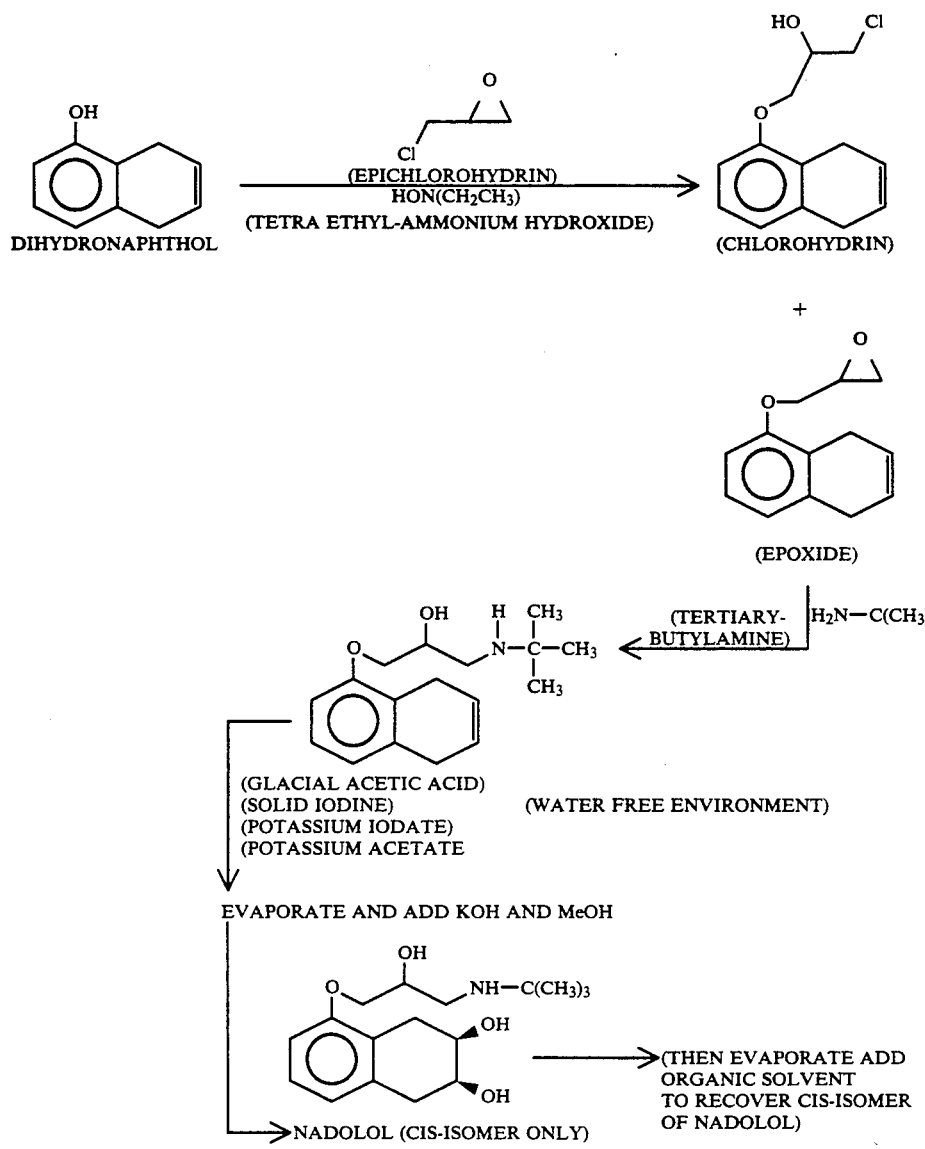

The entire process may be carried out in one reaction vessel not a high pressure reactor Thus Applicant's process may be employed without isolating the epoxide, without using a high pressure reactor, without using silver acetate and without catalytic hydrogenation to produce 5-[d-3-(tert-butylamino)-2-hydroxypropoxy]-1,2,3,4-tetrahydro-1-cis-2,3 naphthalenediol. [Wet acetic acid is to be avoided].

Whereas U.S.P. Nadolol is stated to be 99.4–5% pure, Applicant's invention produces exceptionally pure Nadolol (in the order of at least 99.7% purity) which was found using an in house HPLC method, to exceed U.S.P specification.

In this regard the impurities include new impurity

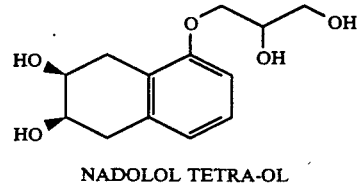

NADOLOL TETRA-OL

The impurities of the process consist essentially of: new impurity

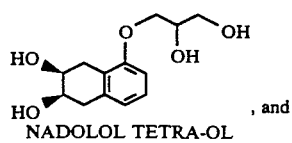

NADOLOL TETRA-OL
, and

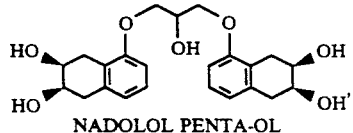

NADOLOL PENTA-OL

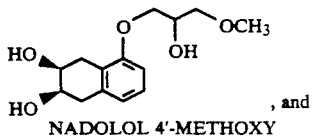

, and

NADOLOL 4'-METHOXY

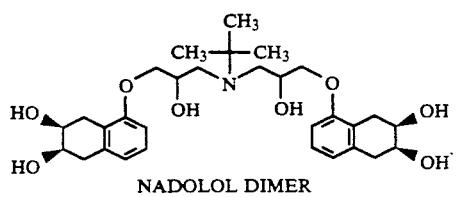

NADOLOL DIMER

DETAILED DESCRIPTION OF PREFERRED EMBODIMENTS OF THE INVENTION

PROTECT FROM LIGHT 1.46 kg 5,8-dihydronaphthol 80% pure (10 mol) is suspended in 9.4 L epichlorohydrin ([9.4/92.53]1.183=12 mol). Purge with nitrogen and add 368 mL tetraethylammonium hydroxide (5 mol%). Heat the reaction to 80° C. and maintain for 2.5 hours. Distill epichlorohydrin completely under vacuum. Add 80 gm methanol, 50 gm water and then 1.5 kg t-butylamine (CAUTION: EXOTHERMIC). Reflux for 6 hours and stir at Room Temperature overnight. Distill off solvent under vacuum. To the thick oil add 3 L chloroform, 2 L water and 0.3 L of a 50% solution of NaOH. Agitate vigorously for 10 minutes and separate. Wash the organic layer with 2 L water. Dry the organic layer over sodium sulfate and evaporate chloroform completely at 80° C. under vacuum.

To the thick brown oil in an essentially water free environment add 12.5 L glacial acetic acid, heat to 60° C. and add 473 g. potassium iodate under nitrogen with good stirring. Add 1.15 kg iodine (4.5 mol) and keep at 60°-75° C. for three hours. Add 1.01 kg potassium acetate and reflux for 1 hour. Evaporate acetic acid completely under vacuum. Add a solution of 3 kg potassium hydroxide dissolved in 9 L methanol and reflux for 5 hours and stir overnight.

Distill off the solvent under vacuum. Cool to Room Temperature and add 7 L of toluene, chloroform or chosen ketone. Agitate vigorously for 15 minutes and separate. Wash the aqueous layer with 3 L chloroform, toluene or chosen ketone. Wash the combined organic extracts with 2×1 L brine. Separate and evaporate the toluene, chloroform, or ketone as the case may be later completely under vacuum. Add 5 L acetone, seed with 5 g Nadolol, and stir for 4 hours. Add another 4 L acetone and stir overnight. Filter crude Nadolol and recrystallize from methanol-acetone and filter. Dissolve crude product in 5 L hot methanol and treat with 100 g active charcoal overnight. Filter and recrystallize from methanolacetone. Filter and wash with 0.5 L acetone. The purity of the product obtained was 99.7%.

The impurities comprise new impurity

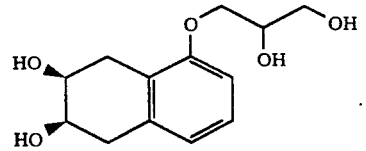

NADOLOL TETRA-OL

The impurities of the process consist essentially: new impurity

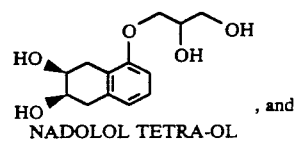

, and

NADOLOL TETRA-OL

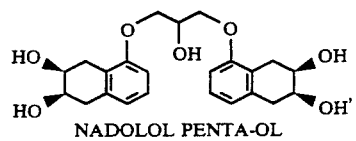

NADOLOL PENTA-OL

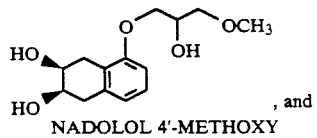

, and

NADOLOL 4'-METHOXY

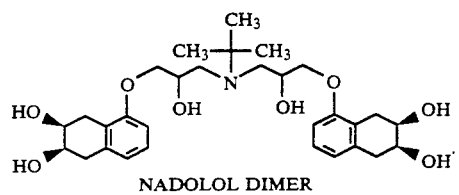

NADOLOL DIMER

Unexpectedly, the elimination of water from the reaction solutions used to make Nadolol from (I) (unlike the processes taught in Canadian Letters Patent 1,064,965 at pages 18 to 20) produces 5-[d-3-(tert-butylamino)-2-hydroxypropoxy]-1,2,3,4-tetrahydro-1-cis-2,3 naphthalenediol. Unexpectedly the yields are high (greater than about 40%) and the purity of the final product exceeds the order of 99.7%.

As many changes can be made to the embodiments without departing from the scope of the invention, it is intended that all material contained herein be interpreted as illustrative of the invention and not in a limiting sense.

The embodiments of the invention in which an exclusive Property or Privilege is claimed are as follows:

1. A process for making 5-{d-3-(tert-butylamino)-2-hydroxypropoxy}-1,2,3,4-tetrahydro-1-cis-2,3 naphthalenediol of the formula

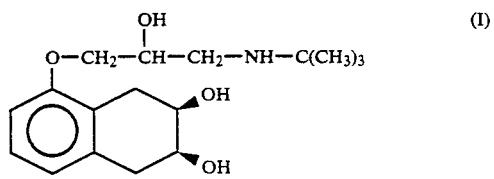

(I)

by reacting

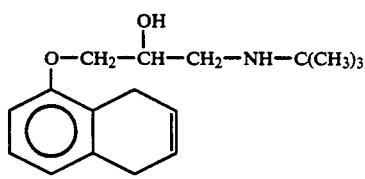
(II)

in an essentially water free environment with
(a) M'IO$_3$ wherein M' represents a suitable ion for forming the salt.

(b) I$_2$ (iodine)
(c) CH$_3$COO$^-$M''$^+$ wherein M'' represents a suitable ion for forming the salt
(d) glacial acetic acid and
(e) ROH/M'''OH where R is alkyl and M''' is a suitable metal ion.

2. The process of claim 1 wherein M', M'' and M''' are each selected from potassium and sodium.

3. The process of claim 1 wherein R is CH$_3$.

4. The process of claim 2 wherein R is CH$_3$.

5. The process of claim 1 wherein

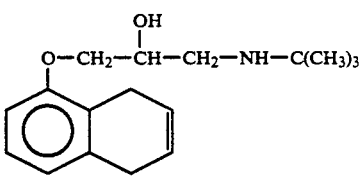
(II)

is manufactured according to the following process

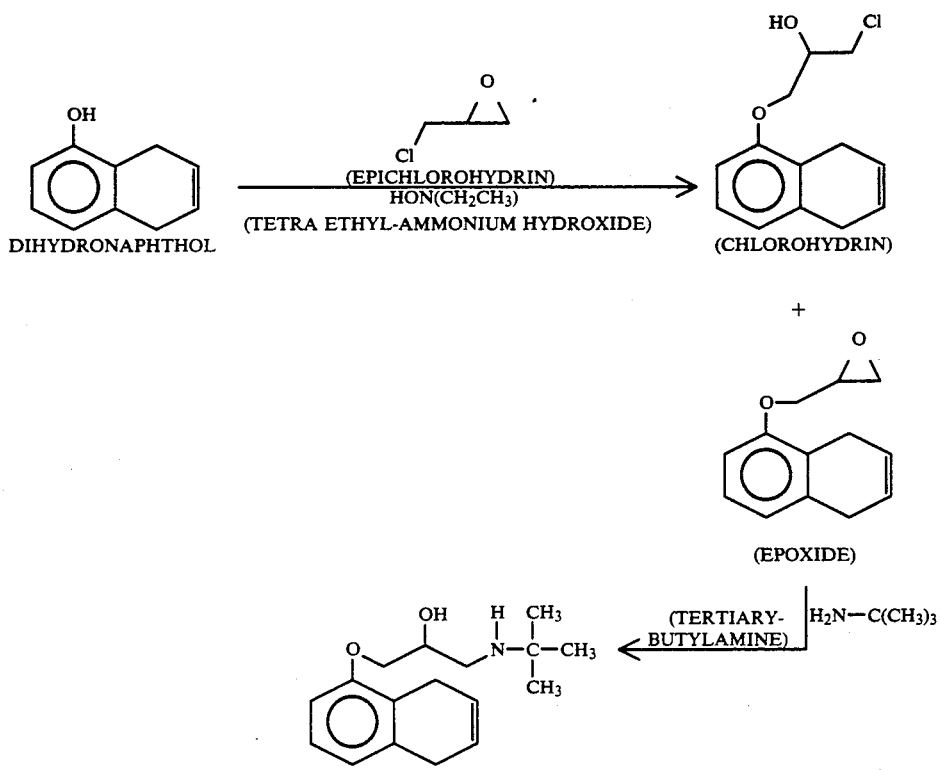

6. The process of claim 2 wherein

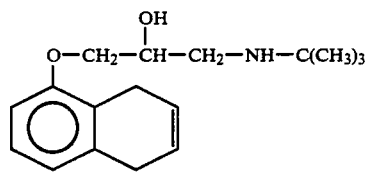

is manufactured according to the following process

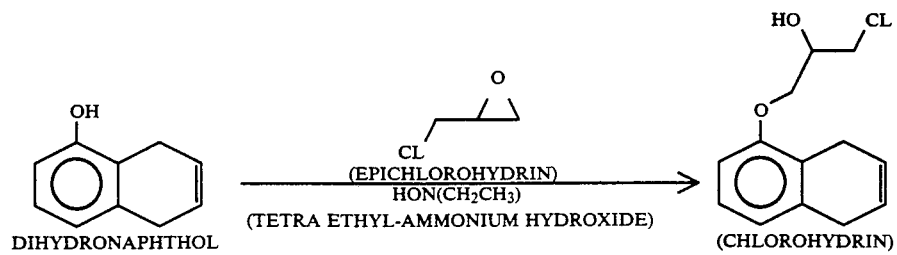

-continued
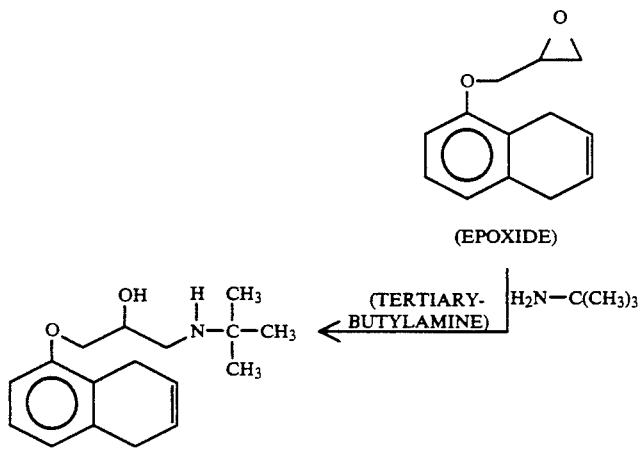
(EPOXIDE)
7. The process of claim 3 wherein
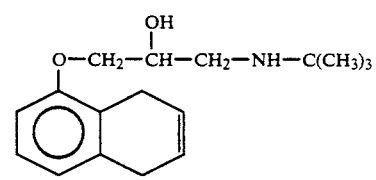
is manufactured according to the following process
8. The process of claim 4 wherein
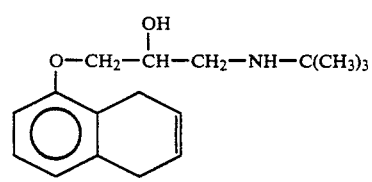
is manufactured according to the following process
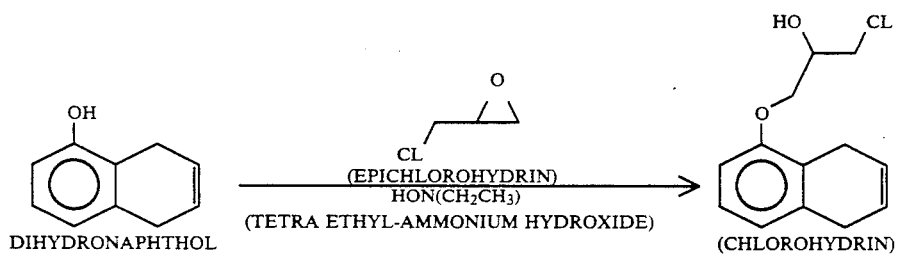
+
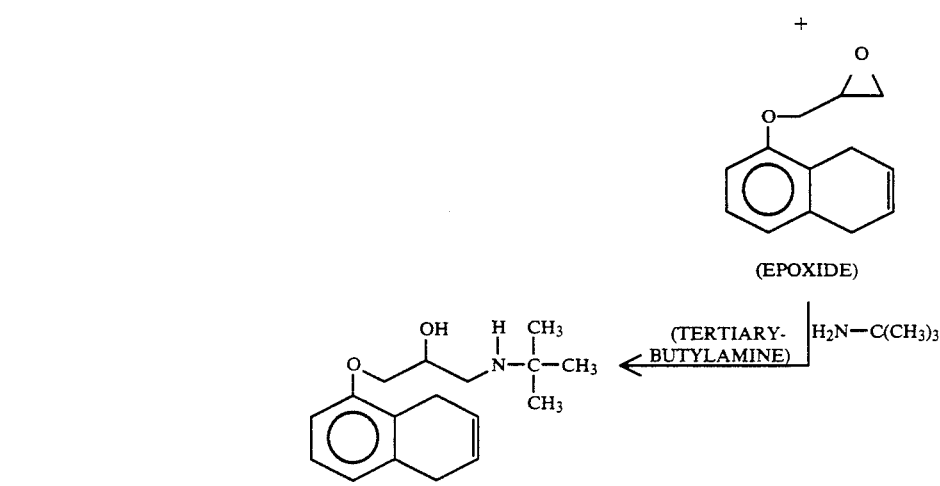

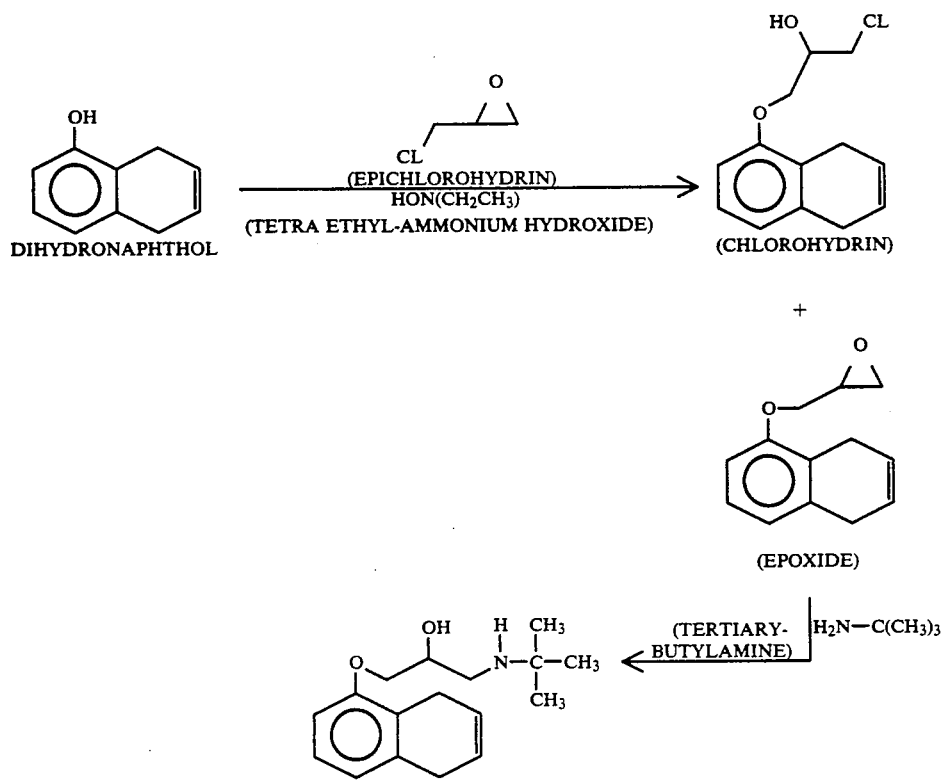
9. A process for directly making the cis-isomer of Nadolol, the process comprising carrying out the following steps:
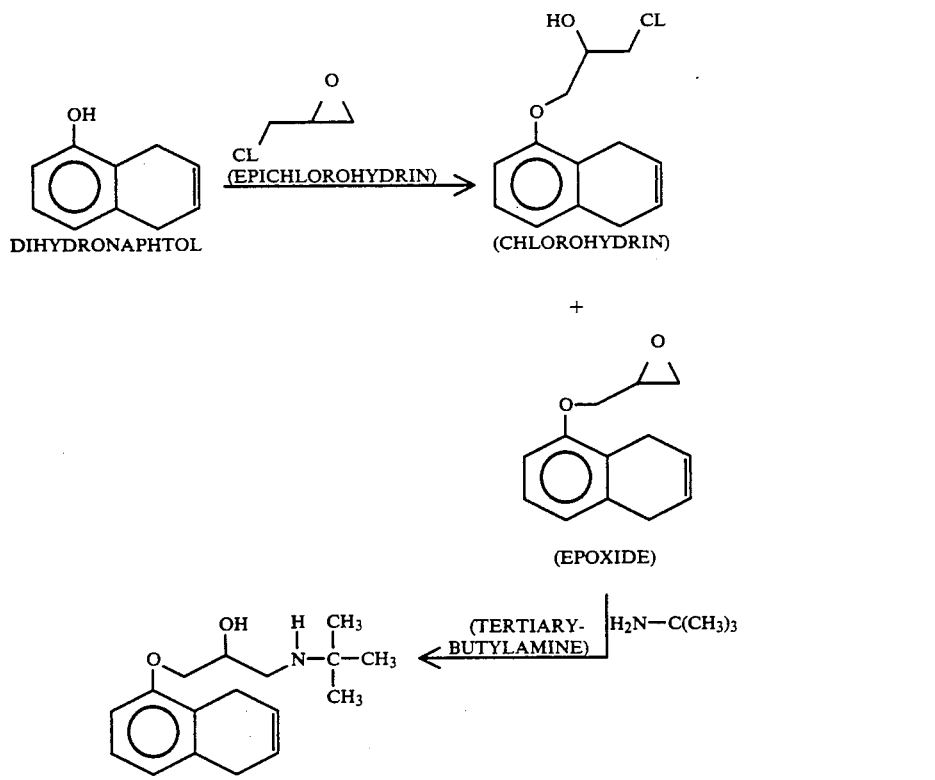

-continued to which has been added (A) (GLACIAL ACETIC ACID)
(B) (IODINE)
(C) (M' IO₃ WHEREIN M' REPRESENTS A SUITABLE ION FOR FORMING THE SALT)
(D) (CH₃COOM" WHEREIN M" REPRESENTS A SUITABLE ION FOR FORMING THE SALT)
(E) ROH/M'''OH WHEREIN R MAY BE AN ALKYL RADIAL AND M''' IS A SUITABLE METAL ION FOR FORMING THE FINAL PRODUCT

} WATER FREE ENVIRONMENT

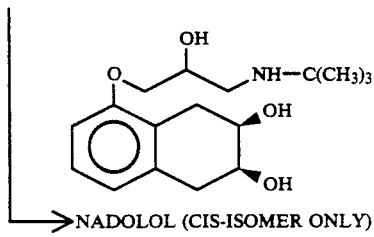

→ NADOLOL (CIS-ISOMER ONLY)

10. The process of claim 9 wherein M', M" and M''' are selected from K⁺ and Na⁺.

11. The process of claim 9 wherein R is methyl.

12. The process of claim 10 wherein R is methyl.

13. A process for directly making the cis-isomer Nadolol, the process comprising carrying out the following steps:

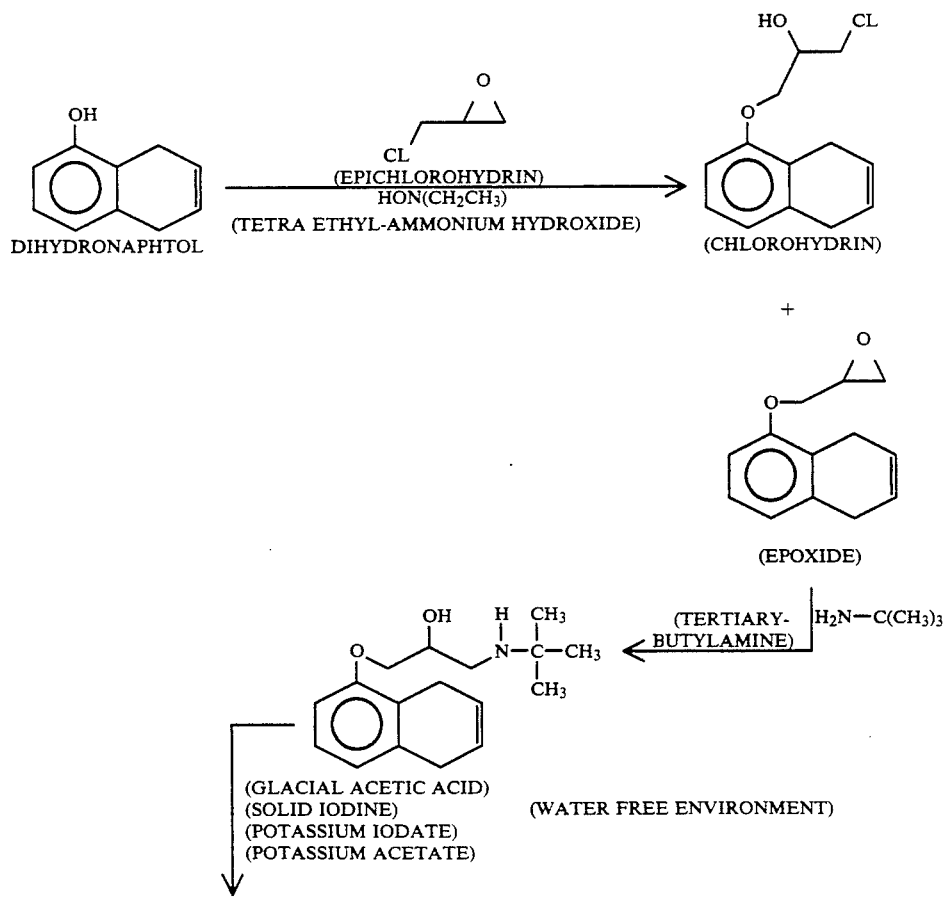

-continued
EVAPORATE AND ADD KOH AND MeOH
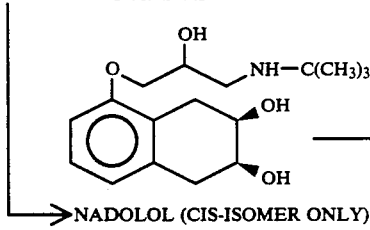
→ (THEN EVAPORATE ADD ORGANIC SOLVENT TO RECOVER CIS-ISOMER OF NADOLOL)
→ NADOLOL (CIS-ISOMER ONLY)
* * * * *